US006981969B2

(12) United States Patent
Chavez et al.

(10) Patent No.: US 6,981,969 B2
(45) Date of Patent: Jan. 3, 2006

(54) ORTHOGONAL ARTERIAL CATHETER

(75) Inventors: Saturnino Chavez, West Point, NY (US); Steven C. Walker, Waxahachie, TX (US); John M. Shepherd, San Antonio, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/442,923

(22) Filed: May 22, 2003

(65) Prior Publication Data
US 2003/0199850 A1 Oct. 23, 2003

Related U.S. Application Data

(63) Continuation of application No. 09/782,607, filed on Feb. 14, 2001, now Pat. No. 6,610,045.

(60) Provisional application No. 60/182,199, filed on Feb. 14, 2000.

(51) Int. Cl.
*A61M 25/00* (2006.01)
*A61M 5/178* (2006.01)
*A61M 31/00* (2006.01)
*A61M 37/00* (2006.01)

(52) U.S. Cl. ............ 604/523; 604/170.03; 604/288.01; 604/288.02

(58) Field of Classification Search .................. 604/523, 604/533–535, 537–539, 288.01–288.04, 604/164.01, 164.13, 170.03, 174, 179; 600/485, 600/486, 488, 573, 581
See application file for complete search history.

(56) References Cited

U.S. PATENT DOCUMENTS

| 3,942,528 | A | 3/1976 | Loeser |
| 4,014,328 | A | 3/1977 | Cluff et al. |
| 4,533,349 | A | 8/1985 | Bark |
| 4,645,492 | A | 2/1987 | Weeks |
| 4,659,329 | A | 4/1987 | Annis |
| 4,763,648 | A | 8/1988 | Wyatt |
| 5,665,076 | A | 9/1997 | Roth et al. |
| 5,674,201 | A | 10/1997 | Steinman |
| 5,833,662 | A | 11/1998 | Stevens |
| 5,944,697 | A | 8/1999 | Biche |

(Continued)

FOREIGN PATENT DOCUMENTS

EP 0956879 A2 11/1999

OTHER PUBLICATIONS

Anonymous, "Arterial Cannulae" web page printout from http://www.health.adelaide.edu.au/icu/manual/Procedure_d.htm, on Jan. 10, 2000.

(Continued)

*Primary Examiner*—Nicholas D. Lucchesi
*Assistant Examiner*—Catherine S. Williams
(74) *Attorney, Agent, or Firm*—Elizabeth Arwine

(57) ABSTRACT

An orthogonal arterial catheter preferably includes a hub and a cannula. The hub preferably protects the cannula from potential kinking and shearing forces because the cannula upon exiting a patient's body enters the hub. The hub preferably provides a passageway through which the hose travels to a connector piece. The connector piece preferably attaches the device to a fluid line such as an arterial line transducer. In addition, the hub preferably includes a port that provides a channel through which a guide wire or a needle may gain access to the cannula. The hub also may include appendages extending from it to suture to the patient.

22 Claims, 3 Drawing Sheets

U.S. PATENT DOCUMENTS

| | | | |
|---|---|---|---|
| 5,968,011 A * | 10/1999 | Larsen et al. | 604/288.02 |
| 6,132,398 A * | 10/2000 | Bierman | 604/174 |
| 6,139,532 A | 10/2000 | Howell et al. | |
| 6,165,156 A | 12/2000 | Cesarczyk et al. | |
| 6,190,352 B1 | 2/2001 | Haarala et al. | |
| 6,346,084 B1 | 2/2002 | Schnell et al. | |
| 6,482,183 B1 | 11/2002 | Pausch et al. | |
| 6,610,045 B2 * | 8/2003 | Chavez et al. | 604/523 |

OTHER PUBLICATIONS

Anonymous, "Insertion of an Arterial Line," printed from the ICU Au Procedure Manual web page http://medicineau.net.au/clinical/ICU/procedures/artlins.html on Jan. 10, 2000.

Arrow International, Arrow Central Venous Access Systems brochure, 1998.

Arrow International, Peripherally Inserted Central Venous Catheters (PICC) and Midline Catheters brochure, 1999.

Johnson & Johnson Gateway, JELCO I.V. Catheter web page, 2000.

Johnson & Johnson Medical, JELCO*-W I.V. Catheter flyer, 1998.

NIH Clinical Center Nursing Department, " Monitoring Hemodynamic and/or Pulmonary Status Arterial Line," http://www.cc.nih.gov/nursing/arterlhps.html, printed on Jan. 10, 2000.

* cited by examiner

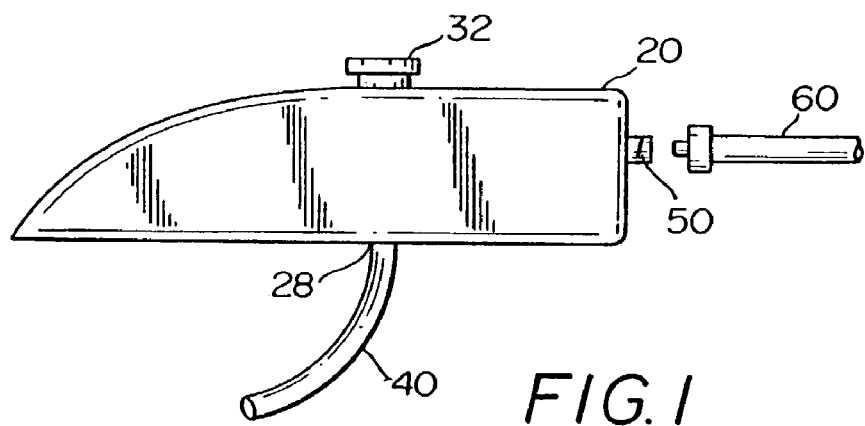
FIG. 1
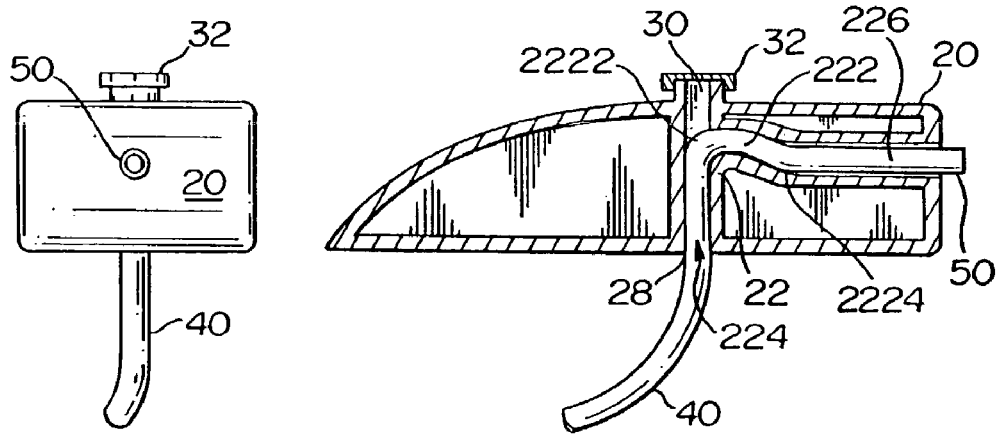
FIG. 2
FIG. 4
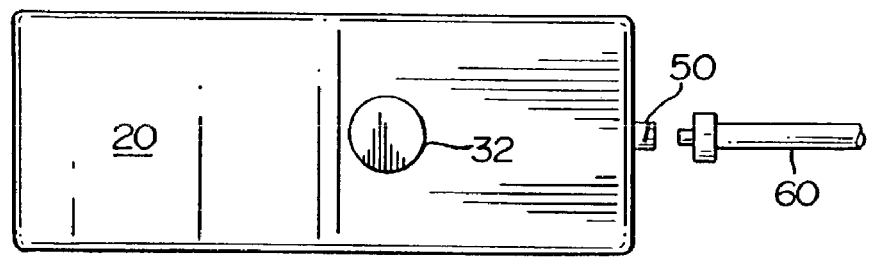
FIG. 3

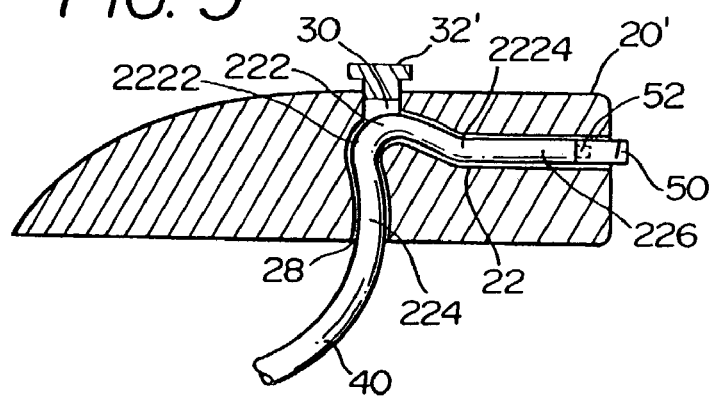
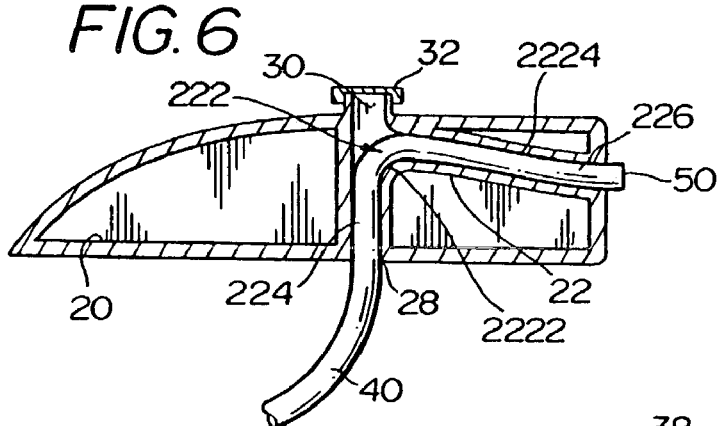
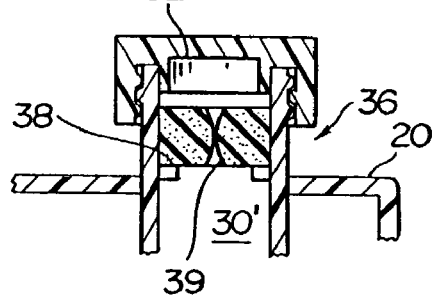
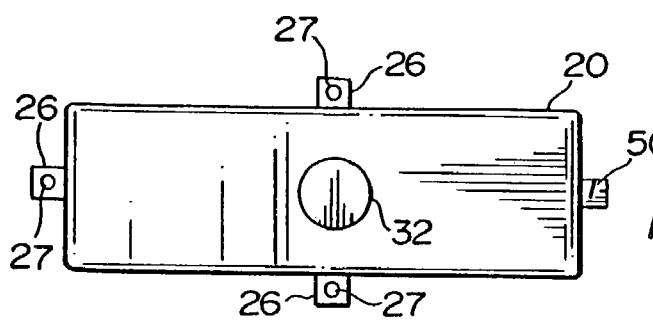
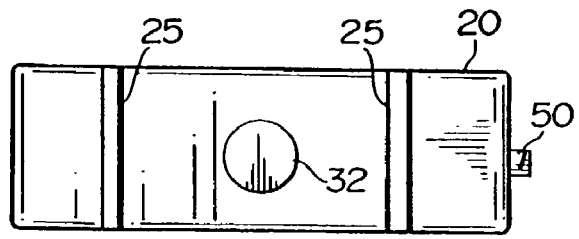

ORTHOGONAL ARTERIAL CATHETER

This application is a continuation of U.S. patent application Ser. No. 09/782,607, filed Feb. 14, 2001, now U.S. Pat. No. 6,610,045, which claims the benefit of U.S. provisional Application Ser. No. 60/182,199, filed Feb. 14, 2000, which are hereby incorporated by reference.

I. FIELD OF THE INVENTION

The invention relates to catheters used to monitor blood pressure within the femoral artery of patients.

II. BACKGROUND OF THE INVENTION

Catheters connecting to blood vessels are used primarily to monitor blood pressure in real-time. When a catheter is inserted into the femoral artery it is done so at a low angle such as 40 to 60 degrees above the skin surface. As the catheter cannula obtains altitude above the patient's body, the cannula is attached to monitoring equipment. The connection point to the monitoring equipment is a place where the catheter will at times shear away from the monitoring equipment, which may result in loss of blood from the patient if the catheter cannula is not quickly removed and/or clamped by medical personnel. The likelihood of shearing is dependent in part upon the firmness of the cannula (or hose) with a firmer cannula more likely to shear. Also, kinking of the cannula may occur, in part, because of the shallow entry angle of the catheter into the patient and movement of the patient's limbs or the catheter itself while obtaining blood samples.

Attempts have been made to use pediatric internal jugular catheters with the femoral artery. This type of catheter cannula also easily shears at the hub causing the catheter cannula to fail because it exits the hub horizontally and then dives beneath the skin into the artery in a somewhat vertical orientation. The pediatric internal jugular catheter also has a long soft Teflon hose, which leads to two additional problems. The length requires that the insertion point be some distance from the hub, which leads to a greater chance of kinking and other problems that may occur when a hose runs for an extended distance unprotected. The second problem is that Teflon is to soft and will collapse in on itself when blood is drawn from the catheter because of the applied suction forces within the hose from the syringe drawing blood. Another problem associated with catheters in general is that it is difficult to obtain accurate blood pressures readings when right angles or kinking occurs in the hose containing the patient's blood, because the kinks and right angles cause turbulence within the blood residing in the cannula.

Usually a catheter is inserted using a needle within a lumen of a cannula. When the needle penetrates the vessel, the blood pressure in the vessel will cause blood to flow up the needle bore and into translucent tubing around the top of the needle. The practitioner verifies the penetration of the vessel by looking for blood "flashback" in the tubing. The needle is withdrawn from the catheter, and the cannula is preferably advanced within the blood vessel to a desired position sometimes with the aid of a guide wire.

Notwithstanding the usefulness of the existing catheters, a need exists for a more dependable and durable catheter that easily attaches to patients and provides real-time accurate blood pressure of the patient.

III. SUMMARY OF THE INVENTION

This invention solves the ongoing problems of attaching a catheter to a patient and obtaining real-time accurate blood pressure. The invention while addressing the problems of the prior art obtains advantages that were not achievable with the prior art devices.

The present invention relates to a catheter capable of being inserted into a variety of veins and arteries as needed by medical personnel who wish and need to monitor a patient's blood pressure in real-time and/or to take regular blood samples from the patient. The invention preferably includes a hub and a cannula running through the hub. The hub preferably provides a port through which to pass a needle and an insertion wire into the cannula and a connector at one end of the cannula/hub to attach to medical equipment. The port may also be used to insert a syringe for obtaining blood samples from the blood present within the hub. The hub preferably includes a passageway that runs from the connector to an exit point through which the cannula travels. The passageway preferably includes a gentle bend to reduce and/or prevent turbulence. The cannula preferably extends from the hub such that it may be inserted into a patient's blood vessel.

An object of this invention is to improve the reliability and accuracy of real-time blood pressure readings.

Another object of this invention is to produce an even and accurate transmission of the blood pressure wave.

Another object of this invention is to lengthen the life span of an inserted catheter by protecting the catheter at the skin insertion site.

Another object of this invention is to increase the ease in which blood samples are taken from patients.

An advantage of this invention is a more secure attachment of the catheter to the patient.

Another advantage of this invention is the durability of the catheter leading to a longer life span for the catheter.

Another advantage of this invention is a lower profile for the device.

Another advantage of this invention is the prevention of turbulence within the catheter.

Given the following enabling description of the drawings, the method should become evident to a person of ordinary skill in the art.

IV. DESCRIPTION OF THE DRAWINGS

The use of cross-hatching within these drawings should not be interpreted as a limitation on the potential materials used for construction of the invention. Like reference numerals in the figures represent and refer to the same element or function.

FIG. 1 illustrates a side view of the preferred embodiment of the invention.

FIG. 2 depicts a front view of the preferred embodiment of the invention.

FIG. 3 illustrates a top view of the preferred embodiment of the invention.

FIG. 4 depicts a side cross-section of the preferred embodiment of the invention.

FIG. 5 illustrates a side cross-section of the preferred embodiment of the invention with an alternative curved passageway.

FIG. 6 depicts a side cross-section of the preferred embodiment of the invention with another alternative curved passageway.

FIG. 7 illustrates a top view of another alternative embodiment of the invention.

FIG. 8 depicts a top view of an alternative embodiment of the invention.

FIG. 9 illustrates a side cross-section of an alternative port configuration.

V. DETAILED DESCRIPTION OF THE INVENTION

FIGS. 1–6 illustrate the preferred embodiment of the invention directed to an orthogonal arterial catheter. The catheter preferably includes a hub 20 and a cannula (or hose) 40. The hub 20 preferably provides the structure to prevent the cannula 40 from kinking on itself and/or shearing from a fluid line 60. The cannula 40 preferably provides the conduit in which blood from the patient resides.

Preferably, the cannula 40 extends sufficiently below the hub 20 such that it may be initially inserted into the patient at a shallow angle to the patient's skin prior to the hub 20 being attached to the patient. Although the length of the cannula 40 preferably will allow the medical professional the whole range of insertion angles. The hub preferably will act as an indicator as to when the cannula has been inserted sufficiently, i.e., when the hub abuts the patient's skin.

Figure 10:
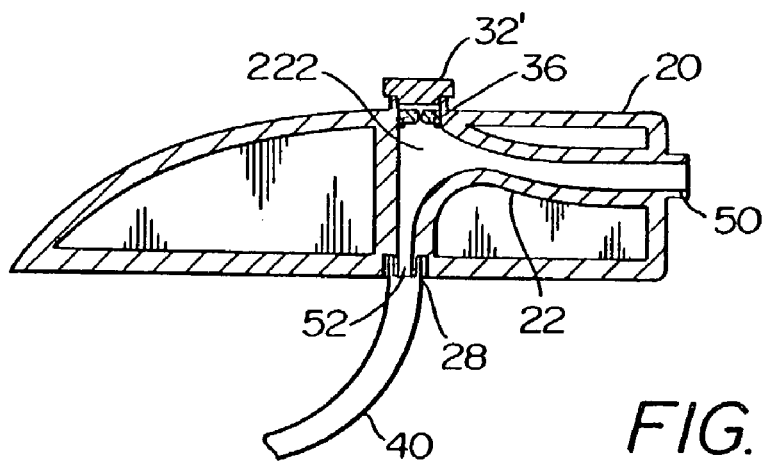
FIG. 10 depicts a side cross-section of another alternative embodiment.
Figure 11:
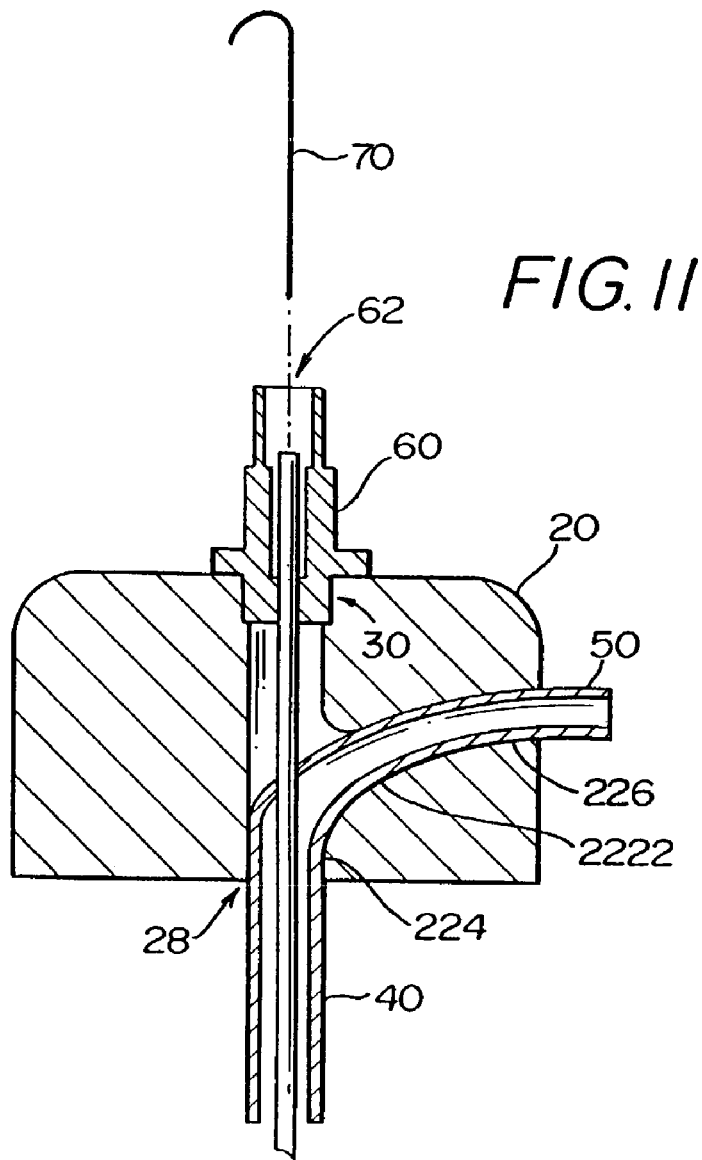
FIG. 11 illustrates a side cross-section of catheter kit that includes the invention.

The hub 20 need not have any particular shape, but preferably it has a bottom surface shaped so it can rest against a patient's body without wobbling. The hub 20 also preferably has a shape such that a user can easily grasp it when the cannula 40 is being installed in a patient's body. The illustrated hub 20 in FIGS. 4 and 6 is a hollow, substantially rigid member having a flat bottom surface and a curving shape on its upper portion. More preferably, the hub 20 is in a shape of a computer mouse (FIGS. 1, 4–6, and 10) or hockey puck (FIG. 11). Alternatively, if the hub 20 is intended to be used in a single location on a patient's body, the bottom surface may be contoured to match the body contour where it is to be installed.

The hub 20 preferably includes a passageway (or channel) 22 and a port 30. Either the hub 20 or the cannula 40 will preferably include a luer-lock connector 50 that will connect to a fluid line 60 (or pressure line). The luer-lock connector 50 preferably is approximately 2 mm to approximately 5 mm above the bottom surface of the hub 20. If the hub 20 includes the luer-lock connector 50, then the luer-lock connector 50 preferably includes a fitting 52 to attach to the cannula 40 to preventing leaking as illustrated, for example, in FIG. 5. Alternatively, the luer-lock connector 50 may be part of the cannula 40 as illustrated, for example, in FIGS. 4 and 6 depending upon the manufacturing design chosen.

The passageway 22 preferably turns from a horizontal alignment at the luer-lock connector 50 to a vertical alignment at the exit point 28 of the cannula 40. In between these two points, the passageway 22 preferably passes through a curved section 222 to change the flow of the hose 90 degrees as illustrated, for example, in FIGS. 4 and 6. FIGS. 4–6, 10, and 11 illustrate different examples for reducing and/or eliminating turbulence resulting from orientation change and pulsation of the blood. Any curve will work that reduces, and preferably eliminates, the turbulence that would occur if the curve was a right angle turn with a "T" being formed by a line from the port 30 to exit 28 and a second line extending from the first line to the luer-lock connector 50. More preferably, the passageway 22 includes a vertical portion 224, a first arcuate portion 2222, a second arcuate portion 2224, and a horizontal portion 226.

The port 30 preferably is directly above and aligned with the hose exit 28 on the hub bottom as shown, for example, in FIGS. 4 and 6. The port 30 preferably is covered with a cap (or valve) 32 that will allow access to the port 30 and thus the cannula 40. The cap preferably is either a rubber stopper 32' or bottle cap 32 with the port 30 having the corresponding top for the desired cap. The cap 32 may lock in place in the port 30 using a luer-lock connection as illustrated, for example, in FIG. 9. The port 30 preferably will allow for the insertion of a guide wire or a needle into the cannula 40, which preferably is self-sealing to prevent leakage of fluid. The needle and/or the guide wire preferably enter the cannula 40 via the port 30 to assist in inserting the cannula 40 into the patient. The port 30 also preferably provides access for inserting a needle or syringe to withdraw blood from the hose for testing without taking blood directly from one of the blood vessels of the patient.

At the luer-lock connector 50, the cannula 40 preferably is adapted to be connected to an external fluid line 60 such as an arterial line transducer. The connection between the luer-lock connector 50 and the fluid line 60 preferably may be either detachable or permanent. In the present example, the luer-lock connector 50 is equipped with a female luer-lock fitting, while the external fluid line 60 is equipped with a male luer-lock fitting for detachably mating with the female fitting. The luer-lock fittings may be reversed between the luer-lock connector 50 and the fluid line 60. A few examples of other types of connections that can be employed to connect the external fluid line at the luer-lock connector include: a bayonet connection, a hose barb connection, or a threaded connection.

The hub 20 and cannula 40 may be integrally formed together such that the hub 20 encases the cannula 40 or the hub 20 may be reusable with different cannulas 40. The hub 20 may be made of any convenient material, such as a metal or plastic. Preferably, the hub 20 is a unitary piece manufactured with the passageway 22 and port 30 such that a cannula 40 with a luer-lock connector 50 may be slid into the passageway 22 as illustrated, for example, in FIGS. 4 and 6.

An alternative is that the hub may include two or more molded sections that can be assembled around the cannula and then secured to each other in any suitable manner. This alternative embodiment is useful when the cannula 40 is inserted into the patient and then is laid over the bottom hub piece. The top hub piece then is placed over the cannula 40 and engages the lower hub piece. The preferable place to divide the hub into two pieces is along the passageway 22.

Another alternative is that the hub and the cannula may be integrally formed with each other. Under any of these designs the hub need not be hollow. For example, the hub 20' may be a solid body of lightweight plastic with the passageway 22 and port 30 formed during molding or bored after formation of the solid body as illustrated in FIG. 5.

The cannula 40 preferably is made from polypropylene, polyvinyl chloride, silicones, fluoropolymer, elastomeric hydrogel, polyurethane, epoxies, polyester, thermoplastics, rubber, similar flexible material, etc. More preferably, the cannula 40 is made of polyurethane. Most preferably, the cannula 40 is made using material capable of resealing after being punctured by a needle. One condition for the cannula material is that it will be able to withstand the vacuum forces resulting from the drawing of blood. A second condition is that the material be able to be inserted into a patient's blood vessel. The cannula 40 does not need to be long, but only of sufficient length to be inserted into a patient's blood vessel sufficiently to redirect some of the blood flow and then reach the fitting and/or luer-lock connector.

Alternatively, the hub 20 may also have attachment sites to secure itself to a patient as illustrated in FIGS. 7 and 8. The illustrated attachment sites are a plurality of tabs 26, which can be sutured or sewn to a patient's body to secure the hub to the patient. Each of the tabs 26 includes a hole 27 through which surgical thread can be passed to suture the hub to a patient's body. However, the attachment sites may be a variety of things that provide a way to attach the hub to the patient preferably through sewn suture. Examples of these types of attachment sites are grooves 25 illustrated in FIG. 8, tunnels, ears, or holes such as eyelets. Different types of attachment sites may be present together on a particular hub. Alternatively, many other items and methods besides surgical thread can be used to immobilize the hub, such as tape, string, or straps.

An alternative structure for the port (or diverting means) 30' is illustrated in FIG. 9. In this alternative embodiment, the port 30' is covered with a sealing mechanism (or preventing blood flow means) 36 that preferably includes a diaphragm 38 of a resilient material (such as an elastomer) which extends across the interior of the port 30' and is sealed around its periphery to the inner wall of the port 30'. The illustrated cap 32 in FIG. 9 may be omitted given the presence of the sealing mechanism 36. The diaphragm (or accessing means) 38 preferably is equipped with a hole (or changing means) 39 through its thickness through which a guide wire, a needle, or other object of relatively small diameter can pass.

When a guide wire or a needle is passed through the hole 39, the resilience of the diaphragm 38 presses the inner wall of the hole 39 sealingly against the outer surface of the guide wire or the needle to prevent fluid from leaking from the port along the exterior of the guide wire or the needle. When the needle or the guide wire is withdrawn from the diaphragm 38, the resilience of the diaphragm 38 completely closes the hole 39 and seals off the port 30. To protect the diaphragm 38 against contamination by substances in the environment or to protect the hospital environment from contamination by fluids withdrawn from the cannula 40 through the diaphragm 38, the port 30 may be equipped with a removable closure such as a cap 32 for covering the diaphragm 38 and the port 30 opening. In the illustrated arrangement in FIG. 9, the cap 32 includes a male luer-lock fitting, which sealingly mates with a female luer-lock fitting on the port 30'.

An alternative structure for the hub and the hose is to have a connection at some place other than at the luer-lock connector when the luer-lock connector is part of the hub 20. The fitting 52 discussed above could be placed at any location within the passageway 22 after the cannula 40 enters the hub 20. However, if the fitting 52 is prior to or at the port intersection with the passageway 22, then the alternative port 30' should be used to prevent blood from flowing out of the hub 20 and thus the patient. FIG. 10 illustrates when the fitting occurs just inside the hub.

Another alternative for the hub is removing the port. The port would be eliminated from the hub when the hub includes a bottom piece and a top piece as described above in a prior alternative embodiment and there is no need to use the hub as the access point to draw blood.

A further alternative embodiment for the invention is to include it in a catheter kit preferably along with a needle (and/or a syringe) 60 and a guide wire 70 as illustrated in FIG. 11. Any combination of the above-described catheter embodiments may be used in this kit. The needle preferably will include a blood flashback compartment 62 and will be hollow. Preferably, the needle will be sufficiently small to be inserted within the cannula 40. The guide wire 70 if included preferably will be of sufficiently small diameter to be inserted through the needle 60.

The above-described device including all of the alternative embodiments preferably are used as follows. The first step is to connect the hub and the cannula together if they are two separate pieces. The second step is to remove the cap from the port. As is readily apparent based on the description above, the first two steps may not be necessary depending upon the design implemented. The third step preferably is to insert a needle through the port into the cannula such that the needle will create a hole through the patient's skin into the selected blood vessel, which preferably is the femoral artery. The fourth step preferably is to guide the cannula into the selected blood vessel of the patient. Preferably, the medical professional will be watching for blood flashback to stop the insertion of the needle any further.

The fifth step preferably is to insert the catheter guide wire through the port into the cannula to further insert the cannula into the patient preferably after at least partial withdrawal of the needle. The fifth step may be omitted depending upon how deep the medical professional wishes to place the cannula into the patient. The fifth step may instead be the simple pushing of the cannula further in by itself without the aid of either a needle or a guide wire. The sixth step preferably is to withdraw the needle and/or catheter guide wire, and replace the cap if one is being used. The seventh step is to connect the fluid line such as an arterial line transducer to the luer-lock connector; however, this step may be performed prior to this time, i.e., with the first or second steps. The eighth step will be to monitor the patient's blood pressure in real-time as this is typically the purpose for installing this type of device.

This method may also include suturing the device in conjunction with the attachment sites to the patient. As discussed above when describing the attachment sites, there are alternative ways to attach this device besides suturing that might be used. The invention is designed such that the medical professional is able to insert the cannula while the hub is above the patient's skin and out of the way.

Once the device is connected to the one of the patient's blood vessels, a blood sample may be taken using the following steps. The first step is to remove the cap, which may or may not be relevant depending on the exact design of the device used. The second step is to insert the syringe or needle through the port into the hose and/or passageway. The third step is to withdraw the desired amount of blood from the hose and/or passageway. The fourth step is to remove the syringe/needle. The fifth step is to replace the cap removed in the first step.

This invention can be used to assist medical professionals in monitoring the blood pressure of a patient in real-time when connected to a fluid transducer while decreasing the risk of having a kink develop in the cannula and/or having the cannula shear its luer-lock connector. This invention is also useful for providing a point from which to draw blood from the patient while the catheter is in use.

Those skilled in the art will appreciate that various adaptations and modifications of the above-described preferred embodiments can be configured without departing from the scope and spirit of the invention. Therefore, it is to be understood that, within the scope of the appended claims, the invention may be practiced and constructed other than as specifically described herein.

We claim:

1. A catheter device for use on a patient, said device comprising:
   a hub having
      a bottom surface formed to rest against the body of the patient,
      at least one side surface,
      a port,
      a passageway passing therethrough said hub, the passageway travels from an opening in said bottom surface of said hub to an opening in said at least one side surface of said hub, the passageway connecting with said port, and
      a plurality of grooves running laterally across said hub.
   a hose in overlapping communication with the passageway beginning at the opening in said bottom surface, and
   a fluid line connector in communication with said hose and the passageway; and.

2. The device according to claim 1, wherein an axis of the passageway at said bottom surface is transverse to an axis of the passageway at said side surface.

3. The device according to claim 1, wherein
   said hose includes said connector, and
   said hose lines the passageway of said hub.

4. The device according to claim 1, further comprising a cover engaging the port of said hub.

5. The device according to claim 1, wherein said hub further includes a sealing mechanism installed in said port to seal off said port from the passageway.

6. The device according to claim 5, wherein said sealing mechanism includes a resilient material having a hole therethrough, said port being closed by the resilience of said sealing mechanism.

7. The device according to claim 1, wherein
   said connector is selected from a group consisting of a luer-lock connector, a bayonet connection, a hose barb connection, and a threaded connection.

8. The device according to claim 1, wherein said hub includes means for attaching to a patient.

9. The device according to claim 1, further comprising a fitting in the passageway of said hub and in communication with said hose, said fitting spaced from said connector.

10. The device according to claim 1, wherein the passageway travels in a plane perpendicular to said bottom surface.

11. A method for using the device of claim 1, comprising:
    connecting the hose and the hub together,
    inserting a needle through the port into the hose,
    guiding the hose into a selected blood vessel of a patient using the needle such that the entire bottom surface is against the skin of the patient and the hub stably rests on the patient,
    withdrawing the needle,
    connecting a fluid line to the connector, and
    monitoring the patient's blood pressure.

12. The method according to claim 11, wherein the selected blood vessel is the femoral artery.

13. A method for obtaining a blood sample using the device according to claim 1 after the device has been installed, the method comprising:
    inserting a syringe through the port into the passageway,
    withdrawing an amount of blood from the passageway, and
    removing the syringe.

14. The device according to claim 1, wherein said hub includes a plurality of tabs extending from at least two side surfaces of said hub, each tab having a hole passing therethrough.

15. A catheter device for use on a patient, said device comprising:
    a hose,
    a connector,
    a hub having
       a bottom surface formed to rest against the body of the patient,
       at least one side surface,
       a port,
       a passageway passing therethrough said hub, the passageway travels from an opening in said bottom surface of said hub to an opening in said at least one side surface of said hub, the passageway connecting with said port, the hose in communication with the passageway, and the connector in communication with said hose and the passageway,
       a top molded section that fits around said hose and includes said port,
       a bottom molded section that fits around said hose,
       said top molded section connects to said bottom molded section such that said bottom surface is formed by the connected sections, and
       the passageway is formed when said top molded section is connected to said bottom molded section.

16. The device according to claim 15, wherein said hub includes a plurality of grooves running laterally across said top molded section of said hub.

17. The device according to claim 15, further comprising a cover engaging the port of said hub.

18. The device according to claim 15, wherein said hub further includes a sealing mechanism installed in said port to seal off said port from the passageway.

19. A catheter device for use on a patient, said device comprising:
    a hub having
       a bottom surface formed to rest against the body of the patient,
       at least one side surface,
       a port, and
       a passageway passing therethrough said hub, the passageway travels from an opening in said bottom surface of said hub to an opening in said at least one side surface of said hub, the passageway connecting with said port,
    a cannula in communication with the passageway, and
    a connector in communication with said cannula and the passageway, said connector includes a fitting in communication with said cannula,
    said hub is integrally formed with said connector, and
    said cannula lines the passageway of said hub from said bottom surface to said fitting.

20. A device comprising:
    a hub having a passageway passing therethrough, wherein the passageway includes:
       a vertical portion,
       a first arcuate portion,
       a second arcuate portion, and
       a horizontal portion; and wherein the vertical portion, the first arcuate portion, the second arcuate portion, and the horizontal portion form a path that provides for minimal turbulence in the flow of blood, a hose in communication with the passageway, a connector in communication with said hose and the passageway; and wherein the passageway travels from an opening in a bottom surface of said hub to an opening in a side surface of said hub.

21. An orthogonal arterial catheter comprising:

a hub having a bottom surface and at least one side surface, said hub including a passageway running from said bottom surface to said at least one side surface in a plane perpendicular to said bottom surface, the passageway having a plurality of arcuate sections, a hose in communication with said hub, and a connector in communication with said hose and said hub; and wherein the surface area of said bottom surface is greater than the surface area of said at least one side surface to which the passageway travels, and said bottom surface is able to rest against the patient and provide stability to the hub.

22. The orthogonal arterial catheter according to claim 21, further comprising a fitting attached to the inside of the passageway passing through said hub, said fitting is in communication with said hose, and said fitting is spaced from said connector.

* * * * *